United States Patent
Swain et al.

(10) Patent No.: US 9,023,113 B2
(45) Date of Patent: May 5, 2015

(54) SYSTEMS FOR INDUCING FLUID FLOW TO STIMULATE TISSUE GROWTH

(71) Applicant: KCI Licensing, Inc., San Antonio, TX (US)

(72) Inventors: Larry D. Swain, San Antonio, TX (US); Michael E. Manwaring, San Antonio, TX (US); Douglas A. Cornet, San Antonio, TX (US); Braden K. Leung, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

(21) Appl. No.: 14/098,195

(22) Filed: Dec. 5, 2013

(65) Prior Publication Data

US 2014/0094928 A1    Apr. 3, 2014

Related U.S. Application Data

(62) Division of application No. 13/466,615, filed on May 8, 2012, now Pat. No. 8,623,086, which is a division of application No. 12/648,453, filed on Dec. 29, 2009, now Pat. No. 8,197,551.

(Continued)

(51) Int. Cl.

| A61F 2/28 | (2006.01) |
|---|---|
| A61M 1/00 | (2006.01) |
| A61M 5/168 | (2006.01) |

(Continued)

(52) U.S. Cl.
CPC ........... *A61F 2/28* (2013.01); *A61F 2002/2817* (2013.01); *A61F 2002/4685* (2013.01); *A61M 1/0088* (2013.01); *A61M 5/16881* (2013.01); *A61M 27/00* (2013.01); *A61M 39/22* (2013.01);

(Continued)

(58) Field of Classification Search
CPC ........................... A61F 2/28; A61F 2002/2821
USPC .................................. 623/16.11, 18.11, 23.49
See application file for complete search history.

(56) References Cited

U.S. PATENT DOCUMENTS

| 1,355,846 A | 10/1920 | Rannells |
|---|---|---|
| 2,547,758 A | 4/1951 | Keeling |

(Continued)

FOREIGN PATENT DOCUMENTS

| AU | 550575 A1 | 3/1986 |
|---|---|---|
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).

(Continued)

*Primary Examiner* — Jason-Dennis Stewart

(57) ABSTRACT

Provided are apparatuses, systems, and methods for treating tissue at a tissue site in a mammal that includes a scaffold adapted to be disposed adjacent to the tissue site and to be fluidly coupled to a blood vessel of the mammal for receiving blood therefrom. Additionally, a scaffold is provided that includes a charged surface comprising a streaming potential.

14 Claims, 3 Drawing Sheets

Related U.S. Application Data

(60) Provisional application No. 61/238,770, filed on Sep. 1, 2009, provisional application No. 61/142,053, filed on Dec. 31, 2008, provisional application No. 61/142,065, filed on Dec. 31, 2008.

(51) Int. Cl.
  *A61M 27/00* (2006.01)
  *A61M 39/22* (2006.01)
  *A61L 27/54* (2006.01)
  *A61F 2/46* (2006.01)

(52) U.S. Cl.
  CPC ..... *A61M 1/0031* (2013.01); *A61M 2205/3334* (2013.01); *A61L 27/54* (2013.01)
  USPC .................................. 623/23.49; 623/16.11

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,030,358 A | 2/2000 | Odland |
| 6,071,267 A | 6/2000 | Zamierowski |
| 6,135,116 A | 10/2000 | Vogel et al. |
| 6,241,747 B1 | 6/2001 | Ruff |
| 6,254,564 B1 | 7/2001 | Wilk et al. |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,008,397 B2 | 3/2006 | Tweden et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2006/0079852 A1 | 4/2006 | Bubb et al. |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 3/1999 |
| WO | 80/02182 A1 | 10/1980 |
| WO | 87/04626 A1 | 8/1987 |
| WO | 90/10424 A1 | 9/1990 |
| WO | 93/09727 A1 | 5/1993 |
| WO | 94/20041 A1 | 9/1994 |
| WO | 96/05873 A1 | 2/1996 |

(56) References Cited

FOREIGN PATENT DOCUMENTS

| WO | 97/18007 A1 | 5/1997 |
|---|---|---|
| WO | 99/13793 A1 | 3/1999 |
| WO | 03/101385 A2 | 12/2003 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, YU. A., et al; "Vacuum Therapy in the Treatment of Purulent Lactation Mastitis"; Vestnik Khirurgi, May 14, 1986, pp. 66-70, and 9 page English translation thereof.
Yusupov. YU. N., et al; "Active Wound Drainage", Vestnik Khirurgi, vol. 138, Issue 4, 1987, and 7 page English translation thereof.
Davydov, YU. A., et al; "Bacteriological and Cytological Assessment of Vacuum Therapy for Purulent Wounds"; Vestnik Khirurgi, Oct. 1988, pp. 48-52, and 8 page English translation thereof.
Davydov, YU. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Dukić, Ž. Maksimović, D. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians (Jul. 2007).
Winet,H. "A Bone Fluid Flow Hypothesis for Muscle Pump-Driven Capillary Filtration: II. Proposed Role for Exercise in Erodible Scaffold Implant Incorporation," European Cells and Materials 2003, vol. 6, pp. 1-11.

SYSTEMS FOR INDUCING FLUID FLOW TO STIMULATE TISSUE GROWTH

CROSS-REFERENCE TO RELATED APPLICATIONS

This application is a divisional of U.S. application Ser. No. 13/466,615, filed May 8, 2012, which is a divisional of U.S. application Ser. No. 12/648,453, filed Dec. 29, 2009, now U.S. Pat. No. 8,197,551, which claims the benefit of U.S. Provisional Application No. 61/238,770, filed Sep. 1, 2009, U.S. Provisional Application No. 61/142,053, filed Dec. 31, 2008, and U.S. Provisional Application No. 61/142,065, filed Dec. 31, 2008, all of which are hereby incorporated by reference.

BACKGROUND

1. Field of the Invention

The present application relates generally to tissue engineering and in particular to scaffolds, systems, and methods suitable for use in treatment of tissue.

2. Description of Related Art

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formation of granulation tissue. Typically, reduced pressure has been applied to tissue through a porous pad or other manifolding device. The porous pad contains pores that are capable of distributing reduced pressure to the tissue and channeling fluids that are drawn from the tissue. The porous pad often is incorporated into a dressing having other components that facilitate treatment. A scaffold can also be placed into a defect to support tissue growth into the defect. The scaffold is usually bioabsorbable, leaving new tissue in its place.

Scaffolds for reduced pressure treatment are described in, for example, WO08/091,521, WO07/092,397, WO07/196, 590, WO07/106,594. The adequacy of current scaffolds for reduced pressure treatment can be evaluated in light of current knowledge of wound healing. Injury to body tissues results in a wound healing response with sequential stages of healing that include hemostasis (seconds to hours), inflammation (hours to days), repair (days to weeks), and remodeling (weeks to months). A high level of homology exists across most tissue types with regard to the early phases of the wound healing process. However, the stages of healing for various tissues begin to diverge as time passes, with the involvement of different types of growth factors, cytokines, and cells. The later stages of the wound healing response are dependent upon the previous stages, with increasing complexity in the temporal patterning of and interrelationships between each component of the response.

Strategies to facilitate normal repair, regeneration, and restoration of function for damaged tissues have focused on methods to support and augment particular steps within this healing response, especially the latter aspects of it. To this end, growth factors, cytokines, extracellular matrix (ECM) analogs, exogenous cells, and various scaffolding technologies have been applied alone or in combination with one another. Although some level of success has been achieved using this approach, several key challenges remain. One main challenge is that the timing and coordinated influence of each cytokine and growth factor within the wound healing response complicate the ability to add individual exogenous factors at the proper time and in the correct coordination pattern. The introduction of exogenous cells also faces additional complications due to their potential immunogenicity as well as difficulties in maintaining cell viability.

Synthetic and biologic scaffolds have been utilized to provide three-dimensional frameworks for augmenting endogenous cell attachment, migration, and colonization. To date, nearly all scaffolds have been designed with the idea that they can be made to work with in situ biology. Traditional scaffolding technologies, however, rely on the passive influx of endogenous proteins, cytokines, growth factors, and cells into the interstitium of the porous scaffold. As such, the colonization of endogenous cells into the scaffold is limited by the distance away from vascular elements, which provide nutrient support within a diffusion limit of the scaffold, regardless of tissue type. In addition, the scaffolds can elicit an immunogenic or foreign body response that leads to an elongated repair process and formation of a fibrous capsule around the implant. Taken together, these complications can all lead to less than functional tissue regeneration at the injury site.

It would therefore be advantageous to provide additional systems to further direct healing and tissue growth. The present invention provides such systems.

SUMMARY

The scaffolds, systems, and methods of the illustrative embodiments described herein are designed to provide active guidance of tissue regeneration through an implanted scaffold. In one embodiment, a system for treating tissue at a tissue site in a mammal is provided that includes a scaffold adapted to be disposed adjacent to the tissue site and to be fluidly coupled to a blood vessel of the mammal for receiving blood therefrom, and a valve adapted to be fluidly coupled to the blood vessel and controllable between an open position and a closed position for regulating the flow of the blood from the blood vessel to the scaffold. In this system, the valve allows the blood to flow from the blood vessel into the scaffold when in the open position and prevents the blood from flowing into the scaffold when in the closed position.

In another embodiment, a system for facilitating growth of tissue at a tissue site of a patient is provided that includes a scaffold adaptable for implantation at the tissue site for providing a structural matrix for the growth of the tissue and further adaptable for being fluidly coupled to a blood vessel of the patient, a valve controllable between an open position and a closed position for regulating the flow of blood from the blood vessel to the scaffold, and a controller operably coupled to the valve to vary the valve between the open position and the closed position. In this system, the valve allows the blood to flow from the blood vessel into the scaffold when in the open position and prevents the blood from flowing into the scaffold when in the closed position.

In an additional embodiment, a scaffold suitable for implantation into a bone defect or fracture is provided that includes a charged surface comprising a streaming potential, wherein, when implanted in a bone defect, electrolytic fluids comprising blood or interstitial fluids from tissue adjacent to the scaffold are drawn across the charged surface of the scaffold by the streaming potential.

In a further embodiment, a method of treating a bone having a defect or fracture is provided that includes implanting the above scaffold into the defect or fracture. Also, a method of modifying a scaffold that is suitable for implantation into a bone defect or fracture is provided that includes inducing a charge onto a surface of the scaffold.

Other objects, features, and advantages of the illustrative embodiments will become apparent with reference to the drawings and detailed description that follow.

DETAILED DESCRIPTION

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
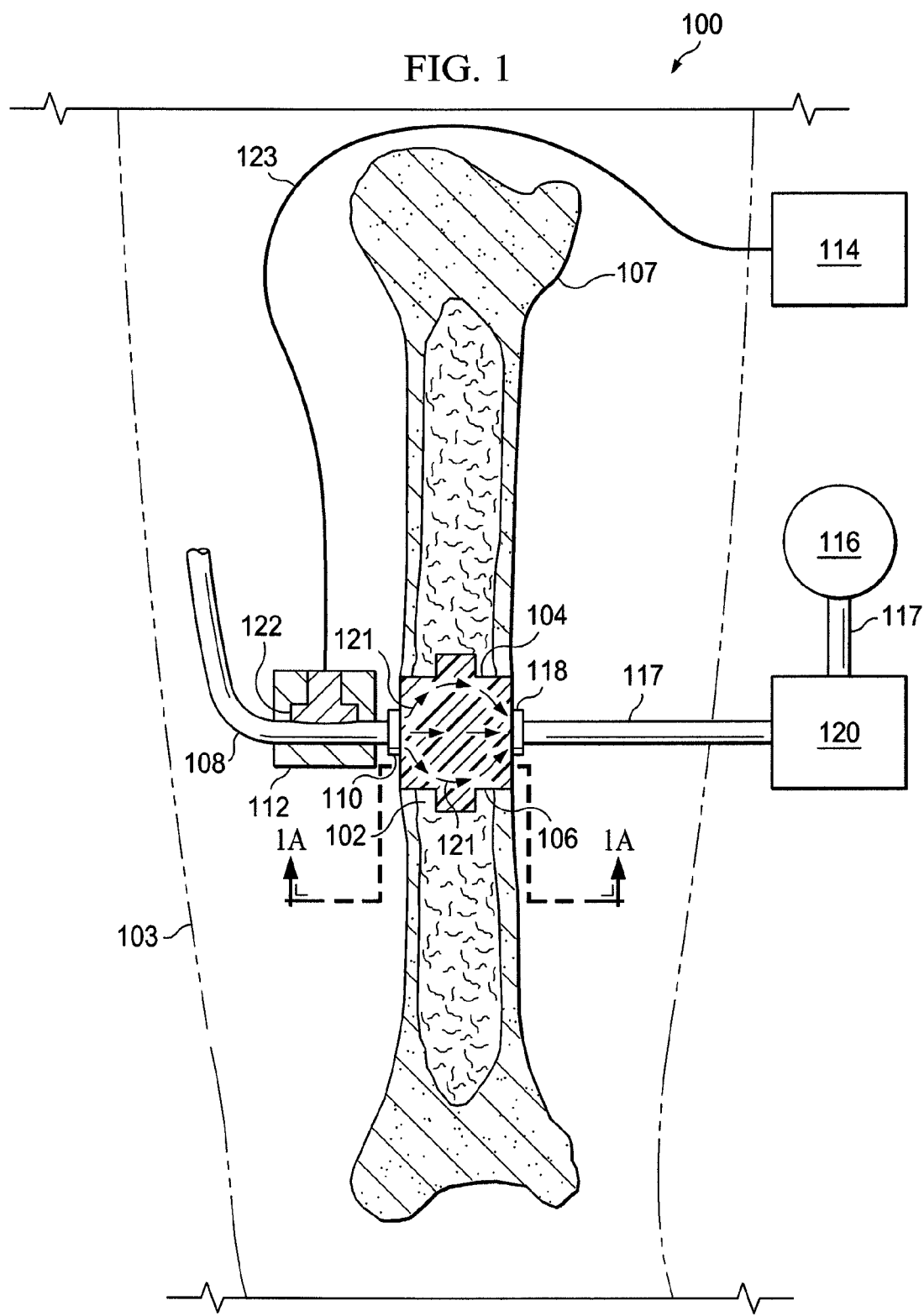
FIG. 1 shows an illustrative embodiment of a reduced pressure therapy system, with a portion shown in cross-section, for treating a tissue site using a scaffold.
Figure 1A:
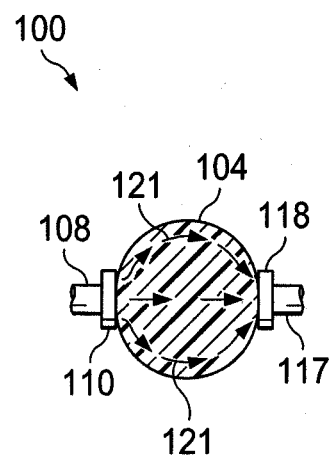
FIG. 1A is a cross-section view of the system of FIG. 1 taken on the line 1A-1A.

Referring to FIGS. 1 and 1A, a reduced pressure therapy system 100 for applying reduced pressure and facilitating the growth of tissue at a tissue site 102 in the body of a patient such as, for example, in a limb 103 of the patient, is shown. The reduced pressure therapy system 100 comprises a scaffold 104 that is implanted in the tissue site 102 to facilitate growth of the tissue at the tissue site 102. In this example, the tissue site 102 may have resulted from a defect or wound 106 in a bone 107 of the patient's limb 103 which contains blood vessels including blood vessel 108. The blood vessel 108 is fluidly coupled to the scaffold 104 via a vessel-scaffold interface 110 to provide a supply of blood to the scaffold 104. The reduced pressure therapy system 100 further comprises a valve 112 to control the supply of blood from the blood vessel 108 to the scaffold 104 and a controller 114 electrically coupled to the valve 112 which is varied between an open and closed position by the controller 114. The blood pressure within the blood vessel 108 forces the blood into the scaffold 104 and the wound site 102 when the valve 112 is opened. Growth and healing of the bone tissue at the wound 106 is enhanced by the various components of the blood including, without limitation, clotting proteins, growth factors, albumin, and lymphocytes, that are supplied to the scaffold 104 and the wound site 102 as the blood begins to flow through the valve 112.

The reduced pressure therapy system 100 may also comprise a reduced pressure source 116 for providing a reduced pressure to the scaffold 104 to draw blood from the blood vessel 108 into the scaffold 104. The reduced pressure source 116 is fluidly coupled to the scaffold 104 via a conduit 117 that is fluidly coupled to the scaffold 104 by a conduit-scaffold interface, or gradient inlet, 118. The conduit-scaffold interface 118 may be a manifold that distributes reduced pressure to the scaffold 104. The reduced pressure therapy system 100 further comprises a canister 120 fluidly coupled between the conduit-scaffold interface 118 and the reduced pressure source 116 to collect bodily fluids, such as blood or exudate, that are drawn from the tissue site 102. Thus, besides drawing blood from the blood vessel 108 into the scaffold 104, the reduced pressure source 116 may also be used to provide reduced pressure therapy to the tissue site 102.

As used herein, the term "coupled" includes direct coupling or indirect coupling via a separate object. The term "coupled" also encompasses two or more components that are continuous with one another by virtue of each of the components being formed from the same piece of material. Also, the term "coupled" may include chemical, mechanical, thermal, or electrical coupling. Fluid coupling means that fluid is in communication between the designated parts or locations.

Upon opening the valve 112, blood flows into the scaffold 104 in various directions as indicated by the arrows 121. The controller 114 and the valve 112 may be used to regulate the volume of blood being supplied to the tissue site 102, such that the blood bathes all or a portion of the scaffold 104 as well as portions of the wound 106. However, the volume of blood flowing through the valve 112 ultimately depends on the blood pressure within the blood vessel 108. Consequently, when the valve 112 is fully open and the blood pressure is too low, the reduced pressure source 116 may be used to apply a reduced pressure to the scaffold 104 to supplement the lower blood pressure. The magnitude and duration of reduced pressure applied to the scaffold 104 by the reduced pressure source 116 may be regulated to achieve the desired pressure and flow through the scaffold 104 in addition to any reduced pressure therapy. In some embodiments, the scaffold 104 includes flow channels (not shown) that direct the blood to specific areas of the scaffold 104, such as those areas where faster scaffold colonization is desired.

The valve 112 comprises a compression member 122 that pushes against the blood vessel 108 to close the blood vessel 108. It should be understood that the compression member 122 may be any type of closure mechanism known to those skilled in the art. Additionally, the valve 112 may be operable between the open and closed position using any type of actuating stimuli, such as pressure (e.g., injecting air or a liquid into the controller 114 through a conduit to close the valve), chemicals such as an oxygen generating reaction, osmotic stimulation, electrical device, an electrically controlled valve, or mechanical device. The valve 112 may include a port (not shown) through which the external stimulus is applied. The valve 112 is operatively connected to the controller 114 via a valve control conduit 123 such as, for example, an electrical conduit, mechanical conduit, or fluid conduit depending on the type of valve utilized.

The reduced pressure therapy system 100 can be used to engineer tissue by providing blood from the blood vessel 108 to the scaffold 104. Growth and healing of the tissue at the wound 106 is enhanced by the various components of the blood including, without limitation, clotting proteins and cells as described above, that are supplied to the scaffold 104 and the wound site 102 as the blood begins to flow through the valve 112. Upon implantation of the scaffold 104, proteins from the blood supplied by the blood vessel 108 can cause a blood clot to form in the scaffold 104 as an initial step in wound healing and tissue formation. Such accelerated clot formation can speed wound healing and tissue formation. In another example, blood is provided to the scaffold 104 later during wound healing or tissue formation, to provide growth factors present in blood that encourage healing and tissue formation. Examples of growth factors in blood include EGF, TGF-α, TGF-β, PDGF, aFGF, and bFGF. Thus, these growth factors are provided to the scaffold 104 with the blood.

Figure 2:
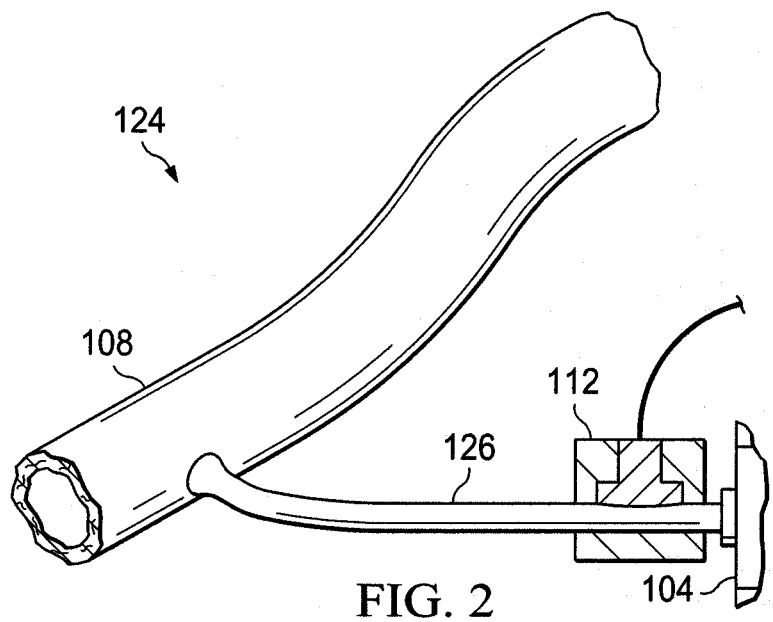
FIG. 2 shows an illustrative embodiment of a portion of a reduced pressure therapy system, with a portion shown in cross-section, for treating a tissue site using a scaffold.

Referring now to FIG. 2, another illustrative embodiment of the reduced pressure therapy system 100 is shown which comprises a blood supply portion 124 that includes a blood vessel 108 that is fluidly coupled to the scaffold 104 by a blood supply conduit 126 rather than being connected directly to the scaffold 104. The blood supply conduit 126 may be a catheter or any other type of biocompatible tubing. The valve 112 controls the flow of blood through the blood supply conduit 126 in the same fashion as described above. Thus, the valve 112 varies between the open and closed positions to control fluid communication between the blood vessel 108 and the scaffold 104. The blood supply portion 124 allows blood to be indirectly supplied to the scaffold 104. In another embodiment, the blood supply conduit 126 is not connected to the blood vessel 108, but rather to an external source of fluids that is located outside of the patient's body (not shown).

The wound 106 may be an injury or defect, such as a fracture, located on or within any type of tissue site 102, including but not limited to, bone tissue, adipose tissue, muscle tissue, neural tissue, dermal tissue, vascular tissue, connective tissue, cartilage, tendons, or ligaments. For example, the wound 106 can include burns, incisional wounds, excisional wounds, ulcers, traumatic wounds, and chronic open wounds. Also, the bone 107 may be any type of bone, including long bones, short bones, flat bones, irregular bones, and sesamoid bones. The wound 106 may also be any tissue that is not necessarily injured or defected, but instead is an area in which it is desired to add or promote growth of additional tissue, such as bone tissue. For example, reduced pressure tissue therapy may be used in certain tissue areas to grow additional tissue that may be harvested and transplanted to another tissue location. The tissue site 102 may also include sites for maintenance of endogenous or exogenous grafts, and supportive scaffolds for subsequent implantation into the patient 103. The patient 103 may be any mammal, such as a mouse, rat, rabbit, cat, dog, or primate, including humans.

In the context of this specification, the term "reduced pressure" generally refers to a pressure that is less than the ambient pressure at a tissue site that is subjected to treatment. In most cases, this reduced pressure will be less than the atmospheric pressure of the location at which the patient is located. Although the terms "vacuum" and "negative pressure" may be used to describe the pressure applied to the tissue site, the actual pressure applied to the tissue site may be significantly greater than the pressure normally associated with a complete vacuum. Consistent with this nomenclature, an increase in reduced pressure or vacuum pressure refers to a relative reduction of absolute pressure, while a decrease in reduced pressure or vacuum pressure refers to a relative increase of absolute pressure. Reduced pressure treatment typically applies reduced pressure at −5 mm Hg to −500 mm Hg, more usually −5 to −300 mm Hg, including but not limited to −50, −125, or −175 mm Hg.

The reduced pressure source 116 may be any device for supplying a reduced pressure, such as a vacuum pump, wall suction, or other source. Also, the reduced pressure may vary in value per change in position to produce three-dimensional reduced pressure gradients throughout the tissue site 102 and scaffold 104. A gradient is a rate of change of a physical quantity that changes in value per change in position. Moreover, the conduit-scaffold interface 118 may be designed to distribute gradients for other physical characteristics, including biologic gradients, thermal gradients, electrical gradients, magnetic gradients, chemical gradients, or positive pressure gradients, each of which may be provided by a suitable gradient source.

Figure 3:
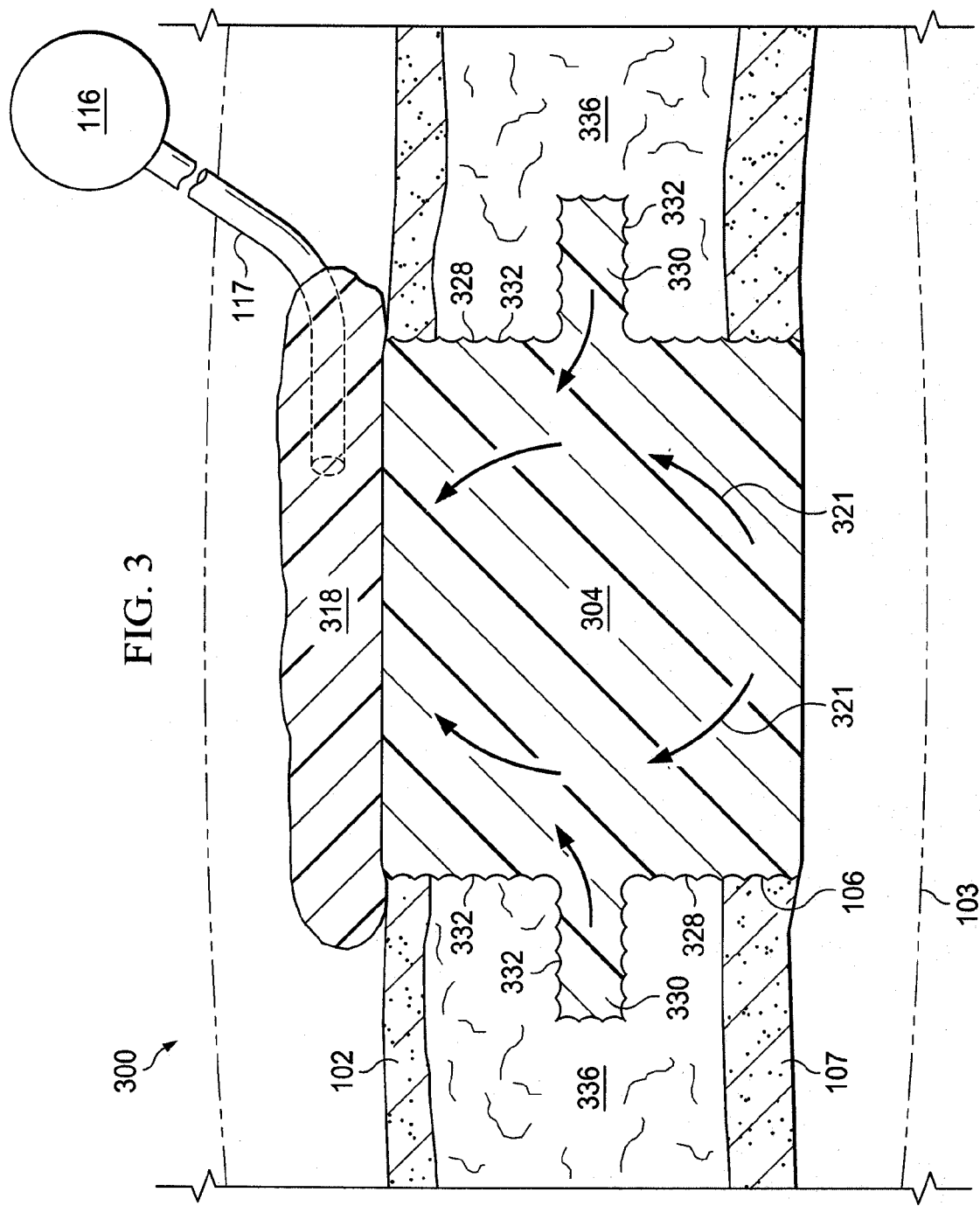
FIG. 3 is a cross-sectional view of a scaffold at a tissue site in accordance with an illustrative embodiment.

Referring to FIG. 3, an alternative embodiment of the reduced pressure therapy system 100 comprising a tissue therapy system 300 that utilizes electrical charge in a modified scaffold 304 similar in structure to the scaffold 104 to facilitate the growth of tissue in the bone 107 of the patient's limb 103. Reduced pressure may be applied to the modified scaffold 304 using the conduit-scaffold interface 118 as a manifold 318 which is fluidly coupled to the reduced pressure source 116 via the conduit 117 as described above. The modified scaffold 304 comprises end surfaces 328 disposed adjacent to the tissue site 102 and intramedullary extensions 330 extending longitudinally therefrom into the intramedullary tissue 336 of the tissue site 102. The end surfaces 328 are charged surfaces so that they draw electrolytic fluid from the tissue adjacent the intramedullary extensions 330 as a result of the streaming potential induced thereon. The charged end surfaces 328 of the modified scaffold 304 may have a texture to enhance the deposition and growth of osteoblasts (Graziano et al., 2007) such as, for example, a texture of concave indentations or concave pits 332 which can be of any size or shape. In some embodiments, the concave pits 332 are 10-120 µm in depth and 3-100 µm in depth.

The charged end surface 328 can be induced by any means known in the art. In some embodiments, the charged surface is induced by electric polarization. See, for example, Nakamura et al., 2006, 2007, 2009; Itoh et al., 2006. The polarization can establish a negative charge or a positive charge on the surface. In various embodiments, the charged surface is negatively charged. Charge also can be applied to the surface by surface treatment by, as an example, changing the surface chemistry to functionalize polymers, such as exposing a hydroxyl (—OH) group.

The tissue therapy system 300 can also cause fluid flow in the scaffold 304 without the use of reduced pressure. A streaming potential can be generated on the charged end surface 328 when an electrolytic fluid, such as blood or interstitial fluid from the tissue site 102, flows past the charged end surface 328. See, for example, Hillsley and Frangos, 1994. The charged end surface 328 can cause the tissue fluids to flow along the charged end surface 328 due to the streaming potential generated therein. A charged surface can induce electroosmotic flow, whereby cations in solution migrate to a charged end, osmotically dragging fluid along with them.

Gradients other than reduced pressure gradients may also be applied to the scaffold 304, including those described above. The gradient provides additional flow at times when increased flow over that generated by the streaming potential is desired, for example, when removal of excess fluid beyond that removed due to the streaming potential is desired. One example of a situation for which additional flow may be desired is any of the initial stages following implantation of the modified scaffold 304.

Using the tissue therapy system 300, a caretaker can apply the modified scaffold 304 to the tissue site 102, and induce a charge at the end surfaces 328, such as by electric polarization. A streaming potential may be induced upon the charged end surface 328 when fluid from the tissue site 102 flows past the charged end surface 328, the streaming potential draws electrolytic fluids comprising blood or interstitial fluids from the tissue site 102 adjacent the modified scaffold 304. If additional fluid flow is desired through the modified scaffold 304, the caretaker may also apply a reduced pressure to the modified scaffold 304 using the manifold 118 and the reduced pressure source 116. Streaming potential, electrolytes moving past a charged surface, also can induce bone formation. Concave surfaces of a charged material in a streaming potential have been shown to form bone while convex surfaces absorb bone (Hillsley and Frangos, 1994).

As indicated above, the conduit-scaffold interface 118 may be a manifold that distributes reduced pressure to the scaffold 104 as shown more specifically in FIG. 3 with reference to the manifold 318. The term "manifold" as used herein generally refers to a substance or structure that is provided to assist in applying reduced pressure to, delivering fluids to, or removing fluids from the tissue site 102. The manifold 318 typically includes a plurality of flow channels or pathways that distribute fluids provided to and removed from the tissue site 102 around the manifold 318. In one illustrative embodiment, the flow channels or pathways are interconnected to improve distribution of fluids provided or removed from the tissue site 102. The manifold 318 may be a biocompatible material that is capable of being placed in contact with tissue site 102 and distributing reduced pressure to the tissue site 102. Examples of manifolds 318 may include, for example, without limitation, devices that have structural elements arranged to form flow channels, such as, for example, cellular foam, open-cell foam, porous tissue collections, liquids, gels, and foams that include, or cure to include, flow channels. The manifold 318 may be porous and may be made from foam, gauze, felted mat, or any other material suited to a particular biological application. In one embodiment, the manifold 318 is a porous foam and includes a plurality of interconnected cells or pores that act as flow channels. The porous foam may be a polyurethane, open-cell, reticulated foam such as GranuFoam®, manufactured by Kinetic Concepts, Inc. of San Antonio, Tex. Other embodiments might include "closed cells." These closed-cell portions of the manifold may contain a plurality of cells, the majority of which are not fluidly connected to adjacent cells. The closed cells may be selectively disposed in the manifold 318 to prevent transmission of fluids through perimeter surfaces of the manifold 318. In some situations, the manifold 318 may also be used to distribute fluids such as medications, antibacterials, growth factors, and various solutions to the wound 106 and the intramedullary tissue 336. Other layers may be included in or on the manifold 318, such as absorptive materials, wicking materials, hydrophobic materials, and hydrophilic materials.

The term "scaffold" as used herein refers to a substance or structure applied to the tissue site 102 that provides a structural matrix for the growth of cells and/or the formation of tissue. The scaffold 104 may be a three-dimensional porous structure that may be infused with, coated with, or comprised of cells, growth factors, extracellular matrix components, nutrients, integrins, or other substances to promote cell growth. The scaffold 104 can also take on characteristics of a manifold by directing flow through the matrix. The scaffold 104 may have a variety of shapes including, for example, a substantially cylindrical shape as shown, a substantially circular shape (not shown, or a rod-shape within the intermeddling tissue of the bone 107 (not shown). In some embodiments, the scaffold 104 is in the shape of a bone defect in the limb 103 of a patient.

Nonlimiting examples of suitable scaffold 104 materials include extracellular matrix proteins such as fibrin, collagen or fibronectin, and synthetic or naturally occurring polymers, including bioabsorbable or non-bioabsorbable polymers, such as polylactic acid (PLA), polyglycolic acid (PGA), polylactide-co-glycolide (PLGA), polyvinylpyrrolidone, polycaprolactone, polycarbonates, polyfumarates, caprolactones, polyamides, polysaccharides (including alginates [e.g., calcium alginate] and chitosan), hyaluronic acid, polyhydroxybutyrate, polyhydroxyvalerate, polydioxanone, polyorthoesthers, polyethylene glycols, poloxamers, polyphosphazenes, polyanhydrides, polyamino acids, polyacetals, polycyanoacrylates, polyurethanes, polyacrylates, ethylene-vinyl acetate polymers and other acyl substituted cellulose acetates and derivatives thereof, polystyrenes, polyvinyl chloride, polyvinyl fluoride, polyvinylimidazole, chlorosulphonated polyolefins, polyethylene oxide, polyvinyl alcohol, Teflon®, hydrogels, gelatins, and nylon. The scaffold 104 can also comprise ceramics such as hydroxyapatite, coralline apatite, calcium phosphate, calcium sulfate, calcium carbonate or other carbonates, bioglass, allografts, autografts, xenografts, decellularized tissues, or composites of any of the above. In particular embodiments, the scaffold comprises collagen, polylactic acid (PLA), polyglycolic acid (PGA), polylactide-co-glycolide (PLGA), a polyurethane, a polysaccharide, a hydroxyapatite, or a polyethylene glycol. Additionally, the scaffold 104 can comprise combinations of any two, three, or more materials, either in separate areas of the scaffold 104, or combined noncovalently, or covalently combined (e.g., copolymers such as a polyethylene oxide-polypropylene glycol block copolymers, or terpolymers), or combinations thereof. Suitable matrix materials are discussed in, for example, Ma and Elisseeff, 2005, and Saltzman, 2004.

In some embodiments, the scaffold 104 comprises a material that is osteoconductive (leads to bone deposition, provided that fully differentiated and competent osteogenic cells are available at the site of implantation) or osteoinductive (induces de novo differentiation of competent osteogenic cells from nonosteogenic and uncommitted cells). Examples of osteoconductive materials include hydroxyapatite, including hydroxyapatite ceramics (Riminucci and Bianco, 2003).

The scaffold 104 can also comprise a living cell. The living cell can be from any organism, including an Archaea, a prokaryote, or a eukaryote. In some embodiments, the cell is a mammalian cell. The cell can be naturally occurring or, alternatively, can be transformed to express a recombinant molecule, for example, a protein or nucleic acid (such as a miRNA). The term "cell" as used herein means any preparation of living tissue (inclusive of primary tissue explants and preparations thereof), isolated cells, cell lines (including transformed cells), and host cells. In some embodiments, autologous cells are employed. In other embodiments, xenogeneic, allogenic, syngeneic cells, or stem cells are used.

These embodiments are not limited to the use of any particular cells. Included herein are any completely differentiated cells, partially differentiated cells (e.g., adult stem cells), or undifferentiated cells (e.g., embryonic stem cells or induced pluripotent stem cells). In some embodiments, the cells are stem cells. These stem cells can be embryonic stem cells. Alternatively, the stem cells can be adult stem cells. Nonlimiting examples of adult stem cells are induced pluripotent stem cells (Takahashi and Yamanaka, 2006), mesenchymal stem cells, adipose-derived adult stem cells, hematopoietic stem cells, mammary stem cells, neural stem cells, endothelial stem cells, olfactory adult stem cells, tooth-derived stem cells, interfollicular stem cells, and testicular stem cells.

The cells can also be, for example, osteoblasts, chondrocytes, fibroblastic cells (e.g., interstitial fibroblasts, tendon fibroblasts, dermal fibroblasts, ligament fibroblasts, cardiac fibroblasts, periodontal fibroblasts such as gingival fibroblasts, and craniofacial fibroblasts), myocyte precursor cells, cardiac myocytes, skeletal myocytes, smooth muscle cells, striated muscle cells, satellite cells, chondrocytes (e.g., meniscal chondrocytes, articular chondrocytes, discus invertebralios chondrocytes), osteocytes, endothelial cells (e.g., aortic, capillary, and vein endothelial cells), epithelial cells (e.g., keratinocytes, adipocytes, hepatocytes), mesenchymal cells (e.g., dermal fibroblasts, mesothelial cells, osteoblasts), adipocytes, neurons, glial cells, Schwann cells, astrocytes, podocytes, islet cells, enterocytes, odontoblasts, or ameloblasts. Different areas of the scaffold 104 can also comprise different cells. For example, the scaffold 104 may be seeded with osteoblasts over most of the scaffold 104 and chondrocytes on a surface of the scaffold 104 where cartilage is desired.

In some embodiments the scaffold 104 further comprises a bioactive agent. A bioactive agent is a compound or element (e.g., iron) that can improve the outcome of the treatment. Examples include nutritional supplements, antibiotics, small (<2000 mw) organic compounds (e.g., serotonin, prostaglandin, prostacyclin, thromboxane, histamine), peptides (e.g., bradykinin), nucleic acids (e.g., aptamers or genetic vectors), and proteins, for example, a cytokine, an enzyme, or a protein comprising an antibody binding site. Other nonlimiting examples of polypeptides that could be included in the scaffold 104 are virtually any hormone, neurotransmitter, growth factor, growth factor receptor, interferon, interleukin, chemokine, cytokine, colony stimulating factor or chemotactic factor protein, or polypeptide. Further examples include transcription or elongation factors, cell cycle control proteins, kinases, phosphatases, DNA repair proteins, oncogenes, tumor suppressors, angiogenic proteins, anti-angiogenic proteins, immune response-stimulating proteins, cell surface receptors, accessory signaling molecules, transport proteins, enzymes, anti-bacterial or anti-viral proteins or polypeptides, and the like, depending on the intended use of the ultimate composition. More specific examples include growth hormone (GH); parathyroid hormone (PTH, including PTH1-34); bone morphogenetic proteins (BMPs) such as BMP-2A, BMP-2B, BMP-3, BMP-4, BMP-5, BMP-6, BMP-7, and BMP-8; transforming growth factor-α (TGF-α), TGF-β1, and TGF-β2; acidic fibroblast growth factor (aFGF); basic fibroblast growth factor (bFGF); granulocyte-colony stimulating factor (G-CSF); granulocyte/macrophage-colony stimulating factor (GM-CSF); epidermal growth factor (EGF); platelet derived growth factor (PDGF); an insulin-like growth factor (IGF); leukemia inhibitory factor (LIF); vascular endothelial growth factor (VEGF); angiogenin; angiopoietin-1; del-1; follistatin; hepatocyte growth factor/scatter factor (HGF/SF); an interleukin including interleukin-8 (IL-8); leptin; midkine; placental growth factor; platelet-derived endothelial cell growth factor (PD-ECGF); platelet-derived growth factor-BB (PDGF-BB); pleiotrophin (PTN); progranulin; proliferin; tumor necrosis factor-α (TNF-α); nerve growth factor (NGF); brain-derived neurotrophic factor (BDNF); B cell-stimulating factor-3 (BSF-3); neurotrophin-3 (NT-3); neurotrophin-4 (NT-4); glia maturation factor (GMF); ciliary neurotrophic factor (CNTF); glial cell-derived neurotrophic factor (GDNF); persephin; neurturin; artemin; growth differentiation factor-9 (GDF9); a matrix metalloproteinase (MMP); angiopoietin 1 (ang1); ang2; and delta-like ligand 4 (DLL4). In some embodiments, the growth factor is growth hormone (GH), a bone morphogenetic protein (BMP), transforming growth factor-α (TGF-α), a TGF-β, a fibroblast growth factor (FGF), granulocyte-colony stimulating factor (G-CSF), granulocyte/macrophage-colony stimulating factor (GM-CSF), epidermal growth factor (EGF), platelet derived growth factor (PDGF), insulin-like growth factor (IGF), vascular endothelial growth factor (VEGF), hepatocyte growth factor/scatter factor (HGF/SF), an interleukin, tumor necrosis factor-α (TNF-α), or nerve growth factor (NGF). The growth factor can be derived from any species, including human.

As described above, the reduced-pressure therapy system 100 applies reduced pressure to the wound 106 which may be distributed uniformly through the scaffold 104. In some embodiments, the scaffold distributes reduced pressure discontinuously through the scaffolds 104 and 304 rather than being distributed in some uniform fashion thereby creating a reduced pressure gradient. For example, the reduced pressure is not delivered uniformly via a single point source, or via a plurality of inlets along a linear flow passage, or through a substantially homogeneous distribution manifold. In some embodiments, the reduced pressure gradient is discontinuous spatially, discontinuous in magnitude, or discontinuous over time. Consequently, the reduced pressure gradients may occur throughout the wound 106.

A gradient is the rate of change of any variable physical quantity in addition to reduced pressure including, without limitation, biologic gradients, thermal gradients, electrical gradients, magnetic gradients, chemical gradients, or positive pressure gradients. The manifolds 118 and 318 and the scaffolds 104 and 304 may be designed to distribute gradients for these other physical characteristics. Referring to FIGS. 1 and 3, for example, the manifolds 118 and 318 and the scaffolds 104 and 304 may distribute reduced pressure gradients and/or biologic gradients as indicated by the arrows 121 and 321, respectively, as described above in more detail and as further described in U.S. Provisional Patent Applications 61/142,053 and 61/142,065, which are hereby incorporated by reference. The circumferential scaffolds 104 and 304 draw fluid radially from the intramedullary space 336 of the bone 107 (not shown) through their respective flow channels as represented by the arrows 121 and 321 in response to the reduced pressure or other stimuli, but in a discontinuous fashion to create gradients to further promote tissue growth and/or tissue healing. Thus, the methods and systems of the present invention provide a means for active guidance of tissue regeneration through the implanted scaffolds 104 and 304 or within a compromised site, such as wound 106, to promote functional recovery utilizing these physical quantity gradients. As such, these methods and systems provide an active mechanism by which to promote the endogenous deposition of proteins and organization of the provisional matrix with biochemical and physical cues to direct cellular colonization of the scaffolds 104 and 304 or tissue space within the wound 106.

References

Anderson E J et al., Tissue Eng. 13:2525-38 (2007).
Anderson E J and Tate M L K, Tissue Eng. 13:2525-2538 (2007).
Brody S and Pandit A, J Biomed Mater Res B Appl Biomater. 83:16-43 (2007).
Gemmiti C V and Guldberg R E, Tissue Eng. 12:469-79 (2006).
Graziano A et al., PLoS ONE 2(6):e496 (2007).
Hillsley M V and Frangos J A, Biotechnol. Bioeng. 43:573-581 (1994).
Itoh S et al., Calcif. Tissue Int. 78:133-42 (2006).
Ma P X and Elisseeff J, ed. Scaffolding in Tissue Engineering, CRC, ISBN 1574445219 (2005).
Manwaring M E et al., Biomaterials 22:3155-3168 (2001).
Manwaring M E et al., Biomaterials 25:3631-3638 (2004).
Mercier et al., Biomaterials 26:1945-1952 (2005).
Mikos A G et al., J. Biomed. Mater. Res. 27:183-189 (2004).

Nakamura M et al., J. Biomed. Mater. Res. A 79:627-34 (2006).
Nakamura M et al., J. Biomed. Mater. Res. N Appl. Biomater. 82:29-36 (2007).
Nakamura S et al. J. Mater. Sci. Mater. Med. 20:99-103 (2009).
Norman J J and Desai T A, Ann Biomed Eng 34:89-101 (2006).
Riminucci M and Bianco P, Braz. J. Med. Biol. Res. 36:1027-1036 (2003).
Saltzman W M, Tissue Engineering: Engineering Principles for the Design of Replacement Organs and Tissues, Oxford ISBN 019514130X (2004).
Sachlos E and Czernuzka J T, Eur. Cells and Mat 5:29-40 (2003).
Segvich S et al., J. Biomed Mater Res B: Appl. Biomater 848:340-349 (2008).
Shimko D A et al., J Biomed Mater Res B: Appl Biomater 73:315-24 (2005).
Takahashi K and Yamanaka S, Cell 126: 663-76 (2006).
Tan S D et al., Bone 41:745-751 (2007).
Tan S D et al., Biochem Biophys Res Comm 369: 1150-1154 (2008)/
Walsh J F et al., Tissue Eng. 11:1085-1094 (2005).
Wen X et al., pp. 1-23 in Handbook of Nanostructured Biomaterials and Their Applications in Nanobioechnology, H. S. Nalwa, ed. ISBN 1-58883-033-0 (2005).
PCT Patent Publication WO06/004951.
PCT Patent Publication WO07/092,397.
PCT Patent Publication WO07/106,594.
PCT Patent Publication WO07/196,590.
PCT Patent Publication WO08/091,521.
U.S. Patent Publication US 2003/0225347.
U.S. Patent Publication US 2008/0033324.
U.S. Patent Publication US 2008/0208358.
U.S. Pat. No. 4,787,906.
U.S. Pat. No. 6,103,255.
U.S. Pat. No. 6,365,146.
U.S. Pat. No. 6,696,575.
U.S. Pat. No. 7,160,553.
U.S. Pat. No. 7,384,786.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

In view of the above, it will be seen that the several advantages of the invention are achieved and other advantages attained. As various changes could be made in the above methods and compositions without departing from the scope of the invention, it is intended that all matter contained in the above description and shown in the accompanying drawings shall be interpreted as illustrative and not in a limiting sense.

We claim:

1. A scaffold suitable for implantation into a bone defect or fracture, the scaffold comprising a charged surface adapted to have a streaming potential,
wherein, when implanted in a bone defect, electrolytic fluids comprising blood or interstitial fluids from tissue adjacent to the scaffold are drawn across the charged surface of the scaffold by the streaming potential.

2. The scaffold of claim 1, further comprising a gradient inlet that provides a gradient to the scaffold.

3. The scaffold of claim 2, wherein the gradient inlet is a reduced pressure inlet.

4. The scaffold of claim 1, wherein the charged surface is induced by electric polarization.

5. The scaffold of claim 1, wherein the charged surface is induced by surface treatment.

6. The scaffold of claim 1, wherein the charged surface is negatively charged.

7. The scaffold of claim 1, wherein the surface of the scaffold further comprises concave pits.

8. The scaffold of claim 7, wherein the concave pits are 10-120 µm in depth and 3-100 µm in depth.

9. The scaffold of claim 1, wherein the scaffold comprises hydroxyapatite or polylactide-co-glycolide (PLGA).

10. The scaffold of claim 1, wherein the scaffold further comprises a cell.

11. The scaffold of claim 10, wherein the cell is an osteoblast or a stem cell.

12. The scaffold of claim 1, wherein the scaffold further comprises a bioactive agent.

13. The scaffold of claim 12, wherein the bioactive agent is a growth factor or an antibiotic.

14. The scaffold of claim 12, wherein the bioactive agent is growth hormone (GH), a bone morphogenetic protein (BMP), transforming growth factor-α (TGF-α), TGF-β, a fibroblast growth factor (FGF), granulocyte-colony stimulating factor (G-CSF), granulocyte/macrophage-colony stimulating factor (GM-CSF), epidermal growth factor (EGF), platelet derived growth factor (PDGF), insulin-like growth factor (IGF), vascular endothelial growth factor (VEGF), hepatocyte growth factor/scatter factor (HGF/SF), an interleukin, tumor necrosis factor-α (TNF-α) or nerve growth factor (NGF).

* * * * *